(12) United States Patent
Belyaev et al.

(10) Patent No.: US 9,771,575 B2
(45) Date of Patent: Sep. 26, 2017

(54) METHODS FOR ON-ARRAY FRAGMENTATION AND BARCODING OF DNA SAMPLES

(71) Applicant: Agilent Technologies, Inc., Santa Clara, CA (US)

(72) Inventors: Alexander Belyaev, San Diego, CA (US); Nicholas M. Sampas, San Jose, CA (US); Alicia Scheffer-Wong, San Jose, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 14/745,174

(22) Filed: Jun. 19, 2015

(65) Prior Publication Data

US 2016/0369266 A1    Dec. 22, 2016

(51) Int. Cl.
| | | |
|---|---|---|
| C12Q 1/68 | (2006.01) | |
| C12N 15/10 | (2006.01) | |
| C12N 9/12 | (2006.01) | |
| C07H 21/04 | (2006.01) | |

(52) U.S. Cl.
CPC ................................ C12N 15/1065 (2013.01)

(58) Field of Classification Search
None
See application file for complete search history.

(56) References Cited

U.S. PATENT DOCUMENTS

| | | | |
|---|---|---|---|
| 2008/0057546 A1 | 3/2008 | Lexow | |
| 2010/0120098 A1 * | 5/2010 | Grunenwald | ........... C12N 15/10 435/91.2 |
| 2011/0312529 A1 | 12/2011 | He et al. | |
| 2012/0053063 A1 | 3/2012 | Rigatti et al. | |
| 2013/0203605 A1 | 8/2013 | Shendure et al. | |
| 2013/0244886 A1 | 9/2013 | Rigatti et al. | |
| 2014/0031261 A1 | 1/2014 | Goryshin et al. | |
| 2014/0093916 A1 | 4/2014 | Belyaev | |
| 2014/0155295 A1 | 6/2014 | Hindson et al. | |
| 2014/0162897 A1 | 6/2014 | Grunenwald et al. | |
| 2014/0194324 A1 | 7/2014 | Gormley et al. | |
| 2014/0206554 A1 | 7/2014 | Hindson et al. | |
| 2014/0227684 A1 | 8/2014 | Hindson et al. | |
| 2014/0228255 A1 | 8/2014 | Hindson et al. | |
| 2014/0235506 A1 | 8/2014 | Hindson et al. | |
| 2014/0287935 A1 | 9/2014 | Rigatti et al. | |
| 2014/0287963 A1 | 9/2014 | Hindson et al. | |
| 2014/0323316 A1 | 10/2014 | Drmanac et al. | |
| 2014/0342921 A1 | 11/2014 | Weiner | |
| 2014/0357523 A1 | 12/2014 | Zeiner et al. | |
| 2015/0050657 A1 | 2/2015 | Rigatti et al. | |

FOREIGN PATENT DOCUMENTS

| | | | | |
|---|---|---|---|---|
| WO | WO2012061832 | 5/2012 | | |
| WO | WO 2012/106546 | * | 8/2012 | ............ C40B 30/04 |

* cited by examiner

*Primary Examiner* — Nancy J Leith

(57) ABSTRACT

The present disclosure provides methods for barcoding a plurality of DNA samples using a microarray of barcode-containing transposase complexes. In some embodiments, the DNA samples and transposase complexes are present in aqueous droplets on the surfaces of opposing substrates, which allows a single DNA sample droplet to be combined with a single transposase-complex droplet. The barcoded DNA in the combined droplets can be used for any number of purposes, including as templates for amplification and sequencing.

19 Claims, 12 Drawing Sheets

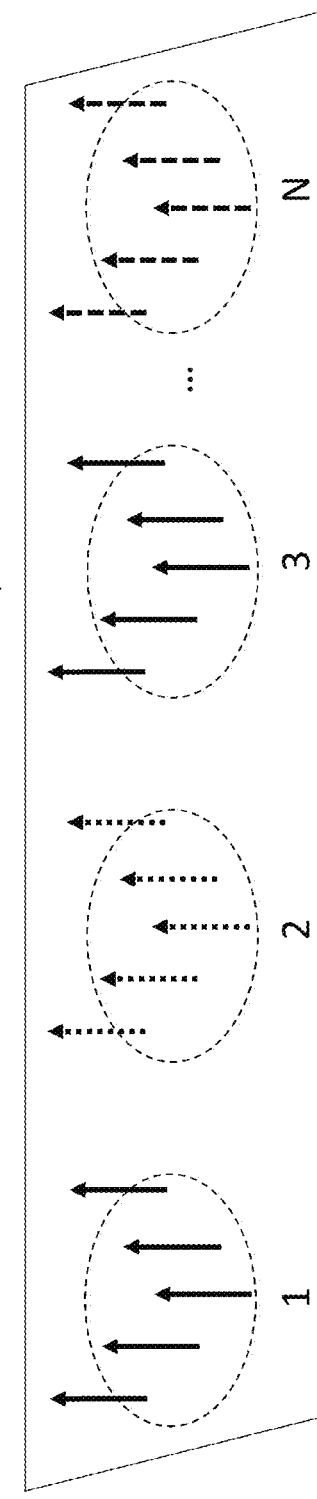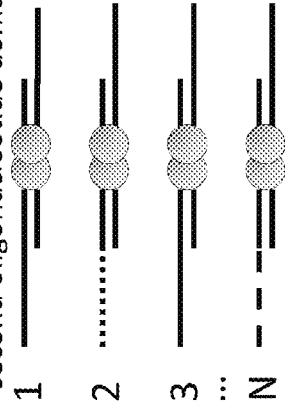
Fig. 3

METHODS FOR ON-ARRAY FRAGMENTATION AND BARCODING OF DNA SAMPLES

FIELD OF THE INVENTION

The present invention relates to the field of molecular biology. More specifically, the invention relates to barcoding DNA in a plurality of DNA samples using corresponding surface-bound transposase complexes.

BACKGROUND

The fragmentation and tagging of DNA (e.g., genomic DNA) is an important step in DNA sample preparation for high-throughput sequencing, also referred to as next generation sequencing (NGS). Earlier sample preparation methods, such as DNA fragmentation using DNAse I, are very unreliable and often result in DNA fragmentation that is either insufficient or too extensive. In either case, the yield of DNA fragments of useful size (about 200-800 base pairs (bp)) is low. DNA shearing using sonicators, for example E220 and E220x instruments from Covaris (Woburn, Mass.), provide an alternative. However, such instruments are very expensive (over $100,000 in 2012 prices) and overall DNA shearing is a laborious and multi-stage process. It involves DNA fragmentation, fragments ends repair, first fragments purification, poly-A tailing, adapter ligation, second fragments purification, PCR amplification, and third fragments purification.

A number of steps in this process can be eliminated/combined using oligonucleotide-transposase complexes, such as the NEXTERA™ DNA sample prep kit from Illumina (San Diego, Calif.). Oligonucleotide-transposase complexes can effect both controlled DNA fragmentation and attachment of adapters in a single reaction, which takes only a few minutes. Examples of such transposase complexes include those that contain a dimer of modified Tn5 transposase and a pair of Tn5-binding double-stranded DNA (dsDNA) oligonucleotides containing a 19 bp transposase-binding sequence, or inverted repeat sequence (IR). In the NEXTERA™ system mentioned above, an engineered, non-native 19 bp transposase binding sequence is used, which provides more efficient DNA fragmentation and tagging than the native Tn5 IR sequence. This binding sequence is referred to as "mosaic".

Unlike DNAase, a single molecule of which can generate numerous breaks in a target DNA, the transposase complex is believed to create only one DNA cleavage per complex. Therefore, unlike with DNAse I, the degree of DNA fragmentation is easily controlled during transposase fragmentation by controlling the ratio of transposase complex to target DNA in the reaction mixture. Furthermore, specific nucleotide tags combined with the mosaic sequence can be attached in this transposase-mediated DNA fragmentation process, which is useful for DNA amplification in PCR and attaching the tagged DNA fragments to sequencing chips.

Given the ever increasing capabilities of NGS technologies to sequence and deconvolute thousands of different barcoded DNA samples mixed in the same sequencing reaction, there is a need in the art to provide improved methods for transposase-mediated barcoding and fragmentation of multiple individual DNA samples. The present disclosure provides methods and compositions that find use in this, and other, applications.

SUMMARY

This invention provides oligonucleotide microarrays with a plurality of immobilized transposase complexes and methods of using the same for barcoding a plurality of DNA samples.

Aspects of the present disclosure include methods of tagging DNA in a plurality of DNA samples, the method comprising: (i) providing a first solid substrate comprising a plurality of features, wherein each of the plurality of features: (a) is in an aqueous droplet; and (b) comprises a substrate-bound transposase complex comprising a first oligonucleotide domain comprising a unique barcode sequence; and (ii) combining the plurality of features on the first solid substrate with a corresponding plurality of DNA samples under conditions that permit transposase-mediated tagging of DNA, wherein each of the plurality of features is combined with a corresponding one of the plurality of DNA samples, and wherein the plurality of DNA samples is present on a second solid substrate, wherein the DNA in each of the of DNA samples is tagged with the unique barcode sequence, thereby producing a plurality of tagged DNA samples.

In certain embodiments, the plurality of features on the first solid substrate are encapsulated in an immiscible liquid.

In certain embodiments, the immiscible liquid is a hydrophobic liquid.

In certain embodiments, the transposase complex in each of the plurality of features is bound to the first solid substrate by hybridization of the first oligonucleotide domain to an oligonucleotide attached to the first solid substrate, wherein the oligonucleotide comprises a sequence complementary to the unique barcode sequence in the first oligonucleotide domain.

In certain embodiments, the providing step (i) comprises: contacting a mixture of transposase complexes with first oligonucleotide domain sequences comprising different unique barcodes with a solid substrate comprising an array of barcode-specific oligonucleotide features under hybridization conditions, thereby producing a solid substrate comprising a plurality of substrate-bound transposase complex features.

In certain embodiments, the mixture of transposase complexes comprises a nuclease inhibitor. In certain embodiments, the nuclease inhibitor is a divalent cation chelating agent. In certain embodiments, the nuclease inhibitor is removed prior to the combining step (ii).

In certain embodiments, each of the DNA samples is in an aqueous droplet. In certain embodiments, the combining step (ii) occurs in an immiscible liquid.

In certain embodiments, the DNA sample is derived from a different source.

In certain embodiments, the DNA sample is derived from a different cell.

In certain embodiments, the method further comprises harvesting and mixing the tagged DNA after the combining step (ii).

In certain embodiments, the plurality of tagged DNA samples is attached to the first solid substrate, the method further comprising contacting the attached plurality of tagged DNA samples to solution-phase transposase complexes comprising a second oligonucleotide domain, wherein the second oligonucleotide domain does not comprise a barcode sequence, thereby tagging the attached plurality of tagged DNA samples with the second oligonucleotide domain.

In certain embodiments, each of the transposase complexes comprises: a first oligonucleotide component comprising a single-stranded region and a double-stranded region, wherein the single-stranded region comprises the first oligonucleotide domain comprising the unique barcode sequence and the double-stranded region comprises a transposase recognition sequence; a second oligonucleotide component comprising a single-stranded region and a double-stranded region, wherein the single-stranded region comprises a second oligonucleotide domain and the double-stranded region comprises a transposase recognition sequence; and a transposase enzyme dimer bound to the transposase recognition sequences of the first and second oligonucleotide components.

In certain embodiments, the first oligonucleotide domain comprises a first primer binding site upstream of the unique barcode sequence and the second oligonucleotide domain comprises a second primer binding site.

In certain embodiments, the method further comprises amplifying the tagged DNA in the plurality of tagged DNA samples using a primer specific for the first primer binding site and/or the second primer binding site, wherein each of the amplified tagged DNA maintains its unique barcode sequence.

In certain embodiments, the amplifying comprises performing a polymerase chain reaction (PCR) with a first and second primer specific for the first and second primer binding sites.

In certain embodiments, the plurality of tagged DNA samples is combined prior to the amplification step.

In certain embodiments, the method further comprises sequencing one or more of the tagged DNA in the plurality of tagged DNA samples.

BRIEF DESCRIPTION OF THE FIGURES

The skilled artisan will understand that the drawings, described below, are for illustration purposes only. The drawings are not intended to limit the scope of the present teachings in any way.

FIG. 3 is a drawing showing the mixture of transposase complexes from FIG. 2 being combined under hybridization conditions with an array of oligonucleotide probes each of which is specific for (complementary to) a first oligonucleotide domain having a specific unique barcode sequence.

DEFINITIONS

Figure 1:
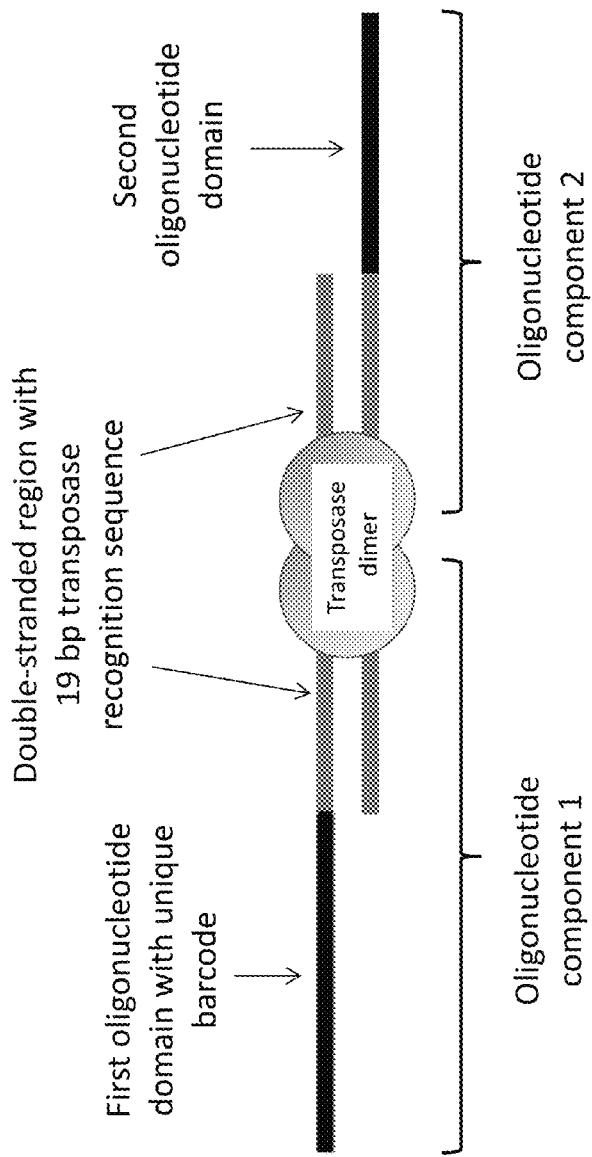
FIG. 1 is a drawing showing certain features of a transposase complex according to aspects of the disclosure.

Before describing exemplary embodiments in greater detail, the following definitions are set forth to illustrate and define the meaning and scope of the terms used in the description.

Numeric ranges are inclusive of the numbers defining the range. Unless otherwise indicated, nucleic acids are written left to right in 5' to 3' orientation; amino acid sequences are written left to right in amino to carboxy orientation, respectively.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

It must be noted that as used herein and in the appended claims, the singular forms "a", "an", and "the" include plural referents unless the context clearly dictates otherwise. For example, the term "a primer" refers to one or more primers, i.e., a single primer and multiple primers. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

As used herein, the terms "array of features", "microarray", and the like are intended to mean a two-dimensional arrangement of addressable regions bearing particular moieties (e.g., biopolymers and/or transposase complexes) associated with that region. Each different addressable region bearing one of more moieties is also called a "feature" (hence the term "array of features"). In some embodiments, an array is an array of polymeric binding agents, where the polymeric binding agents can be any of: peptides, oligonucleotides, polysaccharides, synthetic mimetics of such biopolymeric binding agents, etc. The oligonucleotides of an array can be covalently attached to substrate at any point along the nucleic acid chain, but are generally attached at one terminus (e.g. the 3' or 5' terminus). Sometimes, the arrays are arrays of polypeptides, e.g., proteins or fragments thereof.

Any given substrate can carry one, two, three, four or more arrays disposed on a front surface of the substrate. Depending upon the use, any or all of the arrays can be the same or different from one another and each can contain multiple spots (or features). An array can contain at least, inter alia, 10, at least 100, at least 1,000, at least 10,000, at least 100,000, or at least $10^6$ or more features, in an area of less than 20 cm$^2$, e.g., in an area of less than 10 cm$^2$, of less than 5 cm$^2$, or of less than 1 cm$^2$. In some embodiments, features can have widths (that is, diameter, for a round spot) in the range of, inter alia, from 1 μm to 1.0 cm, although features outside of these dimensions are envisioned. In some embodiments, a feature can have a width in the range of, inter alia, 3.0 μm to 200 μm, e.g., 5.0 μm to 100 μm or 10 μm to 50 μm. Interfeature areas will typically be present which do not carry any polymeric compound. It will be appreciated though, that the interfeature areas, when present, can be of various sizes and configurations.

Each array can cover an area of less than, inter alia, 100 cm$^2$, e.g., less than 50 cm$^2$, less than 10 cm$^2$ or less than 1 cm$^2$. In some embodiments, the substrate carrying the one or more arrays will be shaped generally as a rectangular or square solid (although other shapes are possible), having a length of, inter alia, more than 4 mm and less than 10 cm, e.g., more than 5 mm and less than 5 cm, and a width of more than 4 mm and less than 10 cm, e.g., more than 5 mm and less than 5 cm.

Arrays can be fabricated using drop deposition from pulse jets (or inkjets) of either polynucleotide precursor units (such as monomers) in the case of in situ fabrication, or the previously obtained polynucleotide. Such methods are described in detail in, for example, U.S. Pat. No. 6,242,266, U.S. Pat. No. 6,232,072, U.S. Pat. No. 6,180,351, U.S. Pat. No. 6,171,797, U.S. Pat. No. 6,323,043, U.S. patent application Ser. No. 09/302,898 filed Apr. 30, 1999 by Caren et al., and the references cited therein. These references are hereby incorporated by reference herein. Other drop deposition methods can be used for fabrication, as previously described herein. Also, instead of drop deposition methods, photolithographic array fabrication methods can be used. Interfeature areas need not be present particularly when the arrays are made by photolithographic methods.

An array is "addressable" when it has multiple regions of different moieties (e.g., different polynucleotide sequences) such that each region (i.e., a "feature", "spot" or "area" of the array) is at a particular predetermined location (i.e., an "address") on the array. Array features are typically, but need not be, separated by intervening spaces.

As used herein, the terms "solid substrate", "solid support", and the like, are used in accordance with their meaning in the art. They are thus any material known in the art as suitable for binding and retaining biomolecules, e.g., nucleic acids, under conditions of binding, purification and/or enzymatic reaction. Non-limiting examples of solid substrates useful in the present invention include: nylon, yttrium silicate (YSi), nitrocellulose, PVDF membranes, plastic surfaces (such as those comprising polystyrene or polypropylene), etc. Solid supports can be chemically modified, e.g., aminated (primary or secondary amine) or carboxylated to facilitate attachment of a particular moieties.

The term "nucleotide" is intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the term "nucleotide" includes those moieties that contain hapten or fluorescent labels and can contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like.

The terms "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, up to about 10,000 or more bases composed of nucleotides, e.g., deoxyribonucleotides or ribonucleotides, and can be produced enzymatically or synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine, thymine, uracil (G, C, A, T and U respectively). DNA and RNA have a deoxyribose and ribose sugar backbone, respectively, whereas PNA's backbone is composed of repeating N-(2-aminoethyl)-glycine units linked by peptide bonds. In PNA various purine and pyrimidine bases are linked to the backbone by methylene carbonyl bonds. A locked nucleic acid (LNA), often referred to as an inaccessible RNA, is a modified RNA nucleotide. The ribose moiety of an LNA nucleotide is modified with an extra bridge connecting the 2' oxygen and 4' carbon. The bridge "locks" the ribose in the 3'-endo (North) conformation, which is often found in the A-form duplexes. LNA nucleotides can be mixed with DNA or RNA residues in the oligonucleotide whenever desired. The term "unstructured nucleic acid", or "UNA", is a nucleic acid containing non-natural nucleotides that bind to each other with reduced stability. For example, an unstructured nucleic acid can contain a G' residue and a C' residue, where these residues correspond to non-naturally occurring forms, i.e., analogs, of G and C that base pair with each other with reduced stability, but retain an ability to base pair with naturally occurring C and G residues, respectively. Unstructured nucleic acid is described in US20050233340, which is hereby incorporated by reference herein for disclosure of UNA.

The term "oligonucleotide" as used herein denotes a single-stranded multimer of nucleotides of from about 2 to 200 nucleotides, up to 500 nucleotides in length. Oligonucleotides can be synthetic or can be made enzymatically, and, in some embodiments, are 30 to 150 nucleotides in length. Oligonucleotides can contain ribonucleotide monomers (i.e., can be oligoribonucleotides) and/or deoxyribonucleotide monomers. An oligonucleotide can be, inter alia, 10 to 20, 21 to 30, 31 to 40, 41 to 50, 51-60, 61 to 70, 71 to 80, 80 to 100, 100 to 150 or 150 to 200 nucleotides in length, for example.

The term "primer" as used herein refers to an oligonucleotide, whether occurring naturally or produced synthetically, which is capable of acting as a point of initiation of nucleic acid synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer can be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15-25 or more nucleotides, although it can contain fewer nucleotides. The primers herein are selected to be substantially complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment can be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

The term "adapter" is used herein to refer to an oligonucleotide component, either double-stranded or single-stranded, that is ligated to a polynucleotide using any convenient method. In certain embodiments, an adapter is ligated to a DNA molecule that is being fragmented in a tagmentation reaction with a transposase complex.

As used herein, the term "peptide" is intended to refer to a polymer of amino acids or analogs thereof.

As used herein, the term "organic molecules that have been made by combinatorial chemistry" is intended to refer to an organic polymer that is made using smaller building blocks that are joined to one another to produce a polymer. Such molecules can have a molecular weight of, inter alia, less than 1000 Da, e.g., less than 500 Da, depending on the number of monomers.

An array of polymeric compounds can be made using any suitable method, including methods in which pre-made polymeric compounds are deposited onto the surface of a substrate and then linked to the substrate, and also in situ synthesis methods.

As used herein, the term "synthesizing the polymeric compounds in situ" is intended to refer to methods by which a polymeric compound is grown in place on a substrate using monomeric precursors that are added one by one to a growing chain. Such methods include photolithographic methods, as well as drop deposition methods. Examples of such methods are described in, e.g., Cleary et al. (Nature Methods 2004 1: 241-248) and LeProust et al. (Nucleic Acids Research 2010 38: 2522-2540).

As used herein, the term "bound to the substrate via a cleavable linker" is intended to refer to an arrangement in which a polymeric compound is linked to a substrate via a cleavable bond. A cleavable bond can be cleaved using base (e.g., ammonia or trimethylamine), acid, fluoride or photons, for example.

As used herein, the term "areas that contain the polymeric compounds on the surface of the substrate" is intended to refer to the features that contain the polymeric compounds, as discussed elsewhere herein.

As used herein, the term "remainder of the surface of the substrate" is intended to refer to the areas of the surface of the substrate that do not contain the polymeric compounds (i.e., the areas of the surface of the substrate that lie between the areas that contain the compounds.

As used herein, the terms "hydrophobic" and "hydrophilic" are relative terms and are intended to refer to the degree by which a solution is attracted to or repelled from a surface. Hydrophobicity and hydrophilicity can be measured by measuring the contact angle of the solution on the surface, as described in Johnson et al. (J. Phys. Chem. 1964 Contact Angle Hysteresis 68: 1744-1750). Contact angle is a measure of static hydrophobicity, and contact angle hysteresis and slide angle are dynamic measures. See also the paper entitled Contact Angle Measurements Using the Drop Shape Method by Roger P. Woodward, which can be obtained at the website formed by placing "http://www." in front of "firsttenangstroms.com/pdfdocs/CAPaper.pdf".

As used herein, the term "selectively hydrating" is intended to refer to a step in which an aqueous solution is selectively applied to the areas of an array that contain the polymeric compounds (or selected groups thereof that are immediately adjacent to one another), but not the areas in between those areas. This step results in a substrate that has an array of droplets on its surface, where the edges of the droplets correspond to the boundaries of the features that contain the polymeric compounds.

As used herein, the term "discrete droplets" is intended to refer to droplets on the surface of the substrate that are separated from one another. As described elsewhere herein, each discrete droplet can occupy a single area (i.e., where each droplet lies over a single polymeric compound) or each discrete droplet can occupy multiple areas (where the droplets are actively induced to bleed into each other in a pre-defined way so that one droplet can contain multiple polymers).

As used herein, the term "each droplet contains a single compound" is intended to refer to a droplet that contains multiple molecules of the same substantially pure compound.

As used herein, the term "pre-defined" is intended to refer to something that is known prior to being made.

As used herein, the term "releasing the polymeric compounds from the surface" is intended to refer to a step in which the polymeric compounds are cleaved from the substrate surface. This step is done by cleaving a cleavable linker that links the polymeric compounds to the surface of the array.

As used herein, the term "collecting the droplets in an immiscible liquid" is intended to refer to a step in which droplets that are on the surface of a substrate are physically separated from the substrate to become droplets in an immiscible liquid, i.e., an emulsion.

As used herein, the term "emulsion" is intended to refer to a mixture of two or more liquids that are normally immiscible, in which one liquid forms droplets that are dispersed within another liquid. A water-in-oil emulsion refers to an emulsion that contains aqueous droplets and an organic (oily or hydrophobic) continuous phase. Depending on the liquids used, the droplets of an emulsion can be in the range of, inter alia, 100 nm to 100 µm, e.g., 1 µm to 50 µm.

As used herein, the term "droplet" is intended to refer to the aqueous part of an emulsion that is interspersed in a continuous liquid that is immiscible with water (i.e., the immiscible liquid).

As used herein, the term "immiscible liquid" or "immiscible fluid" is intended to refer to a continuous part of an emulsion.

As used herein, the term "in the solution phase" is intended to refer to a polymeric compound that is in an aqueous environment that is not bound or tethered to a solid substrate. Such a polymeric compound can be dissolved in the aqueous environment.

As used herein, the term "adjacent to one another on the substrate" is intended to refer to areas that contain polymeric compounds that are immediately adjacent to one another (i.e., next to each other, without any other areas that contain polymeric compounds that are in between).

As used herein, the term "mixture" is intended to refer to a solution in which the components are interspersed with one another and not spatially separated.

As used herein, the term "aqueous" is intended to refer to a medium in which the solvent is water.

As used herein, the term "a plurality of molecules of the compound(s)" is intended to refer to a composition that contains multiple molecules of the same compound. For example, a solution containing at least 100 molecules of a compound(s) contains at least 100 molecules of the same compound. More specifically, if a droplet contains at least 100 molecules of a particular oligonucleotide, then it contains at least 100 molecules of the same oligonucleotide.

A "plurality" contains at least 2 members. In certain cases, a plurality can have, inter alia, at least 10, at least 100, at least 1,000, at least 10,000, at least 100,000, at least $10^6$, at least $10^7$, at least $10^8$ or at least $10^9$ or more members.

Other definitions of terms can appear throughout the specification.

DETAILED DESCRIPTION

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

The citation of any publication is for its disclosure prior to the filing date and should not be construed as an admission that the present claims are not entitled to antedate such publication by virtue of prior invention. Further, the dates of publication provided can be different from the actual publication dates which can be independently confirmed.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

All patents and publications, including all sequences disclosed within such patents and publications, referred to in the present disclosure are hereby expressly incorporated by reference herein.

Aspects of this disclosure are drawn to methods for the simultaneous fragmentation and barcoding of distinct DNA samples using small compartments on the surface of a DNA microarray. The combination of fragmentation and barcoding is sometimes called "tagmentation." This approach can be applied to multiple samples, as well as to multiplex single-cell sequencing. It can also be applied to DNA derived from reverse transcription followed by DNA amplification. The approach can be combined with target enrichment schemes, such as Agilent's SureSelect™ and HaloPlex™. Applications include disease diagnostics and cancer genomics for both the research and clinical markets.

In brief, this method combines the droplet encapsulation of transposase complexes loaded with barcoded adapters on the surface of a microarray, the encapsulation of independent samples in droplets attached to a surface or in solution, and the directed combination of these droplets. The methods herein detail combining the sample droplets with the surface droplets as well as the generation of the transposase complex microarray.

FIG. 1 provides a schematic of one example of a transposase complex that finds use in the methods disclosed herein. The complex includes a transposase dimer bound to oligonucleotide components 1 and 2, where oligonucleotide component 1 contains a double-stranded region containing a 19 bp transposase recognition sequence and a first oligonucleotide domain (single-stranded in FIG. 1) and oligonucleotide component 2 contains a 19 bp transposase recognition sequence and a second oligonucleotide domain (also single-stranded in FIG. 1). Each of these components is described in further detail elsewhere herein.

The transposase in the transposase complexes of the present disclosure can be any enzyme having transposase activity in vitro. It can be a naturally occurring transposase or a recombinant transposase. The transposase can be isolated or purified from its natural environment (i.e., cell nucleus or cytosol), at least to some extent. Preferably, the transposase is recombinantly produced, and preferably is isolated or purified from the recombinant host environment (i.e., cell nucleus or cytosol), at least to some extent.

Examples of transposase enzymes that have been shown to have use in NGS processes are hyperactive Tn5, a genetically modified variant of an enzyme from *Shewanella* and *Escherichia* bacteria, phage Mu transposase, and a natural transposase from *Vibrio harveyi* (see US Patent Application Publication US 20140093916 entitled "Immobilized Transpose Complexes for DNA Fragmentation and Tagging", hereby incorporated by reference herein in its entirety). This US patent application Publication also showed that transposase complexes attached to a solid support are active and can fragment DNA to the size required for sequencing on the Illumina platform. Another advantage of *Vibrio harveyi* transposase is its high level recombinant protein expression in soluble form and as such is relatively easy to obtain in a highly purified form. This is especially valuable for single cell barcoding applications, as traces of DNA from recombinant transposase host cells can complicate NGS at low input. The naturally occurring enzyme sequence is available as hypothetical protein VIBHAR-03113 [*Vibrio harveyi* ATCC BAA-1116] under NCBI/GenBank Accession No. YP-001446289, and is sometimes referred to herein at times as "Vibhar".

While the naturally occurring Vibhar transposase is exemplified herein, it is to be understood that other naturally occurring transposases with "cut and paste" mechanisms of insertion (e.g., IS50 transposase, also called Tn5 transposase) are included within the scope of this invention. Furthermore, engineered transposases (e.g., transposase having modified Tn5 transposase sequences), which are derived from naturally occurring transposases but include one or more amino acid deletions, substitutions, or additions, are also encompassed. Further, chimeric transposases are encompassed by the invention. It is to be understood that the modifications made to the naturally occurring transposases do not abolish the transposase activity of the enzyme, although the modifications can alter the specificity or activity in some way. Those of skill in the art can recognize residues that are important in function of the various transposases encompassed by the invention with reference to conserved residues among transposases based on alignment of sequences of transposases.

The transposases according to the invention, when used to fragment DNA, are preferably present in complexes comprised of at least two transposases (as shown in FIG. 1), where at least two of the transposases of each complex are associated with a DNA oligonucleotide component (also shown in FIG. 1). The oligonucleotide components are at least partially double-stranded and contain, in the double-stranded region, a 19 bp transposase recognition sequence. The oligonucleotide components are sometimes referred to herein as "adapters", as they are ligated to the DNA that is being fragmented in the tagmentation reaction. Within the transposase complexes, each transposase can be the same, or have the same recognition sequence for DNA. Alternatively, if the transposases can recognize sequences that differ in several nucleotides, the recognition sequences can differ (see, e.g., see US Patent Application Publication US 20140093916; hereby incorporated by reference herein). Yet again, the two can differ in identity and/or recognition sequences. Where the two transposases have different recognition sequences, the adapters are suitably designed such that each transposase can bind an adapter.

The adapters are bound to the transposases of the complex at double-stranded DNA (dsDNA) regions of the adapters, each of which, as noted elsewhere herein, contain a recognition sequence for the transposase. The different adapters in a particular transposase complex can, but do not necessarily, have the same recognition sequence for a particular transposase. However, in some embodiments, the adapters can have different recognition sequences for the same transposase. Alternatively, where two different transposases are in a transposase complex and each has a different recognition sequence, one adapter of the complex will have the recognition sequence for one of the transposases and the other adapter will have the recognition sequence for the other transposase.

In addition to the dsDNA recognition sequence regions, typically the adapters comprise at least one other region or domain (the first and second oligonucleotide domains as shown in FIG. 1), which can contain specific functional sequences, including barcode sequences or other tags, primer binding sites for amplification or other polymerization reactions, restriction enzyme recognition sites, etc. It is noted here that transposase complexes can be heterodimeric with respect to the first and second oligonucleotide domains, i.e., containing different first and second oligonucleotide domains (as depicted in FIG. 1) or can be homodimeric with respect to the first and second oligonucleotide domains, i.e., containing the same first and second oligonucleotide domains (not shown in FIG. 1). Such design decisions will depend on the desires of the user and/or at which step in the tagging process the transposase complex is employed. The additional region/domain can be either double-stranded or single-stranded or a combination of both. It is a routine task for the skilled artisan to design a primer binding sequence and corresponding primer, and it is left to the practitioner to devise suitable sequences for use in primer binding and extension. Further, it is well within the skill in the art to design primer binding sites that, when employed in downstream processes, will maintain sequences necessary for the desired analysis, e.g., primers that when used to amplify a tagged DNA fragments maintain the barcode tag in daughter DNA species (i.e., the primer site is upstream of the barcode sequence).

In certain embodiments, at least one of the oligonucleotide domains includes a single-stranded region that allows hybridization of the transposase complex to a surface-bound oligonucleotide that is complementary to all or part of the single-stranded region (the first oligonucleotide domain in FIG. 1). Where the first oligonucleotide domain includes a barcode sequence, hybridization of the transposase complex to a surface-bound oligonucleotide is dependent on the presence in the surface-bound oligonucleotide of a sequence complementary to the barcode sequence in the first oligonucleotide domain.

The oligonucleotide components of a transposase complex can be generated in any convenient manner and can take any convenient form. In certain embodiments, an oligonucleotide component is a single DNA molecule that forms a hairpin structure to form the dsDNA region whereas in other embodiments, an oligonucleotide component contains two DNA molecules hybridized to one another to form the dsDNA region.

Figure 2:
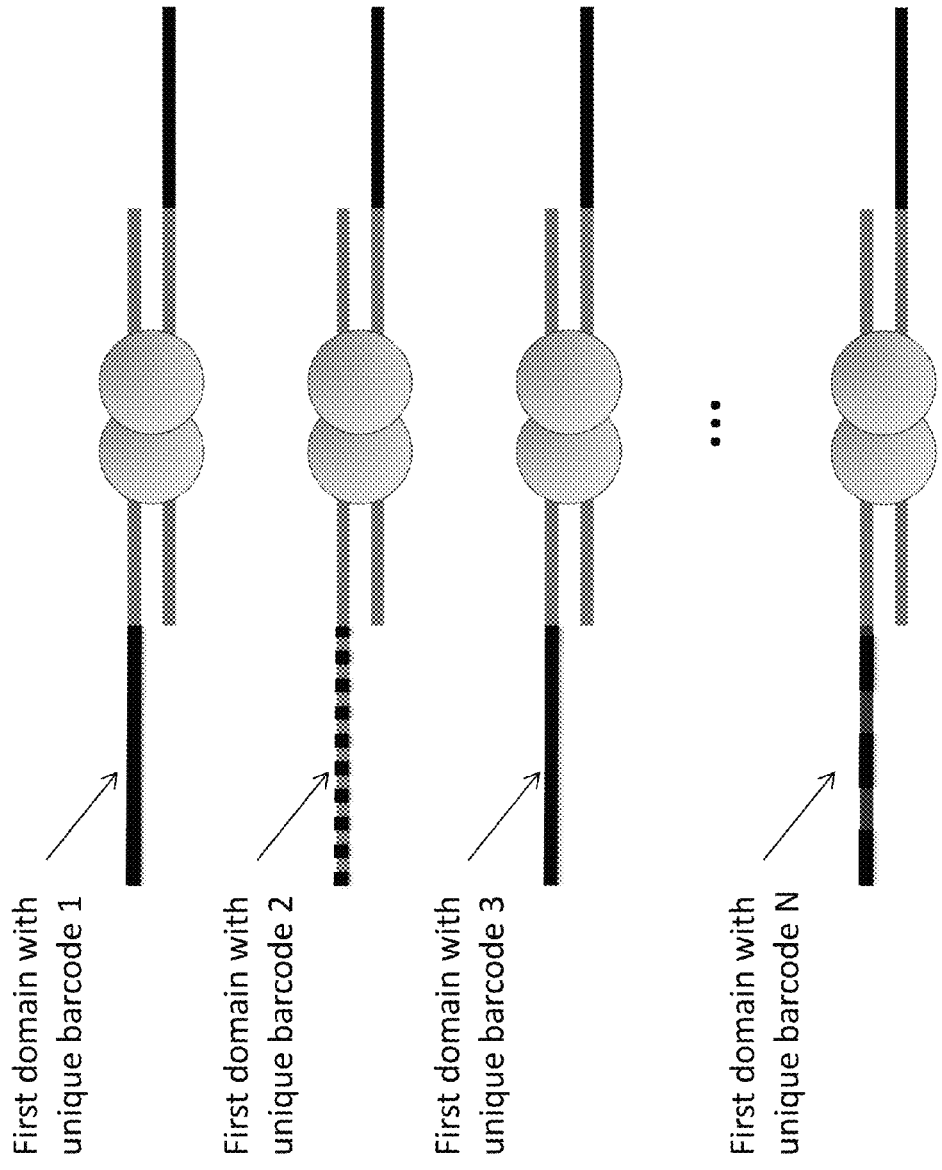
FIG. 2 is a drawing showing a mixture of transposase complexes having first oligonucleotide domains with different unique barcodes.

FIG. 2 shows a mixture of transposase complexes with different barcodes in the first oligonucleotide domain. In each of the complexes shown, the first oligonucleotide domain (single-stranded DNA; ssDNA) includes a unique barcode sequence. Formation of such a mixture of barcodes can be achieved in any convenient manner. For example, the barcode regions can be introduced during the synthesis of the oligonucleotide by including several degenerate sites within the single-stranded region of the first oligonucleotide domain. This single-stranded region is generally in the range of about 10-100 nucleotides, e.g., about 10-80 nucleotides, about 13-60 nucleotides, about 15-40 nucleotides, etc. No limitation in this regard is intended.

It is noted here that in certain embodiments, the single-stranded barcode sequence is not completely degenerate. Thus, different barcodes can differ from each other by only a subset, but not all, of the positions within the barcode sequence (e.g., at one, two, or three positions in a 10 nucleotide barcode sequence). Moreover, some variable positions in the barcode sequence can be partly degenerate, for example differing across a subset by only 2 or 3 of the 4 canonical nucleotides at each degenerate position.

While not shown in FIG. 2, each different transposase complex can be homodimeric, i.e., containing identical adapters having the same barcode domain in the first and second oligonucleotide domains.

Degenerate barcode sequence differences can be generated during synthesis using "degenerate base" sites, where each degenerate base is a specific mixture of nucleotides from which different oligonucleotide molecules will have different nucleotides randomly incorporated into the sequence at each degenerate-base position. In some cases, the nucleotide mixtures can be biased, making some nucleotides more abundant than others. Furthermore, degenerate parts can be designed contingent upon how many barcodes are required and can contain substantial constant parts. The fewer barcodes that are required, the fewer degenerate sites needed. As an extreme example, when only 4 barcodes are required, for example a 21-nucleotide degenerate region can contain constant positions 1-10 and 12-21, with only position 11 being degenerate and having random incorporation of G, A, T, C. If 1000 distinct barcodes are required, then as few as 5 bases ($4^5=1024$ distinct combinations) can be made polymorphic.

Alternatively, a set of oligonucleotides can be generated by pooling discretely synthesized oligonucleotides, either from a batch of distinct syntheses or by cleaving an array of surface-bound oligonucleotides (such as Agilent's OLS library).

Those skilled in the art can design a plurality of degenerate nucleotides that allow their selective hybridization to certain oligonucleotides immobilized on microarrays, as well as to ensure that the hybridization is stable (melting temperature of the hybridized oligonucleotides is well above microarray hybridization temperature).

FIG. 2 shows one embodiment of a mixture of transposase dimer-oligonucleotide complexes that contain both barcode-containing adapters (adapters with the first oligonucleotide domain) and non-barcode containing adapters (adapters with the second oligonucleotide domain). This configuration is one that might be desired by a user (although as noted elsewhere herein, homodimer transposase complexes also find use in DNA tagging).

In certain embodiments, the production of heterodimer transposase complexes (not shown in FIG. 2) is accomplished by asymmetric preloading the transposase with a mixture that will bias toward heterodimer formation. In this approach, the transposase is with an excess of non-barcoded adapters as compared to barcoded adapters, e.g., an excess of 10 times or greater. By using an excess of non-barcoded sequences, three populations of transposase complexes dimers are produced: the largest population having of two copies of the non-barcoded adapter (homodimer 1), the next largest population having one barcoded adapter and one non-barcoded adapter (heterodimer), and the third population (the one we want to minimize) having two copies of a barcoded adapter (homodimer 2; note that the two barcodes in this transposase complex are not necessarily the same).

Yet another method to achieve maximum proportion of heterodimers within a given pool of loaded transposase complexes is to subject the pool to successive rounds of hybridization-based selection. For example, a mixture of homodimer and heterodimer transposase complexes can be subjected to a first hybridization step to isolate molecules comprising sequences present only in the non-barcoded adapter (e.g., a primer binding site or other non-degenerate domain) using surface bound oligonucleotides complementary to these domains. These isolated complexes can be released and the subjected to a second hybridization reaction to isolate complexes containing sequences present only in the barcoded adapter using surface bound oligonucleotides complementary to these domains. It is noted sequences other than those in the barcoded region of the barcode adapter can be used, e.g., a primer binding site that is not present in the non-barcoded adapter).

Figure 4:
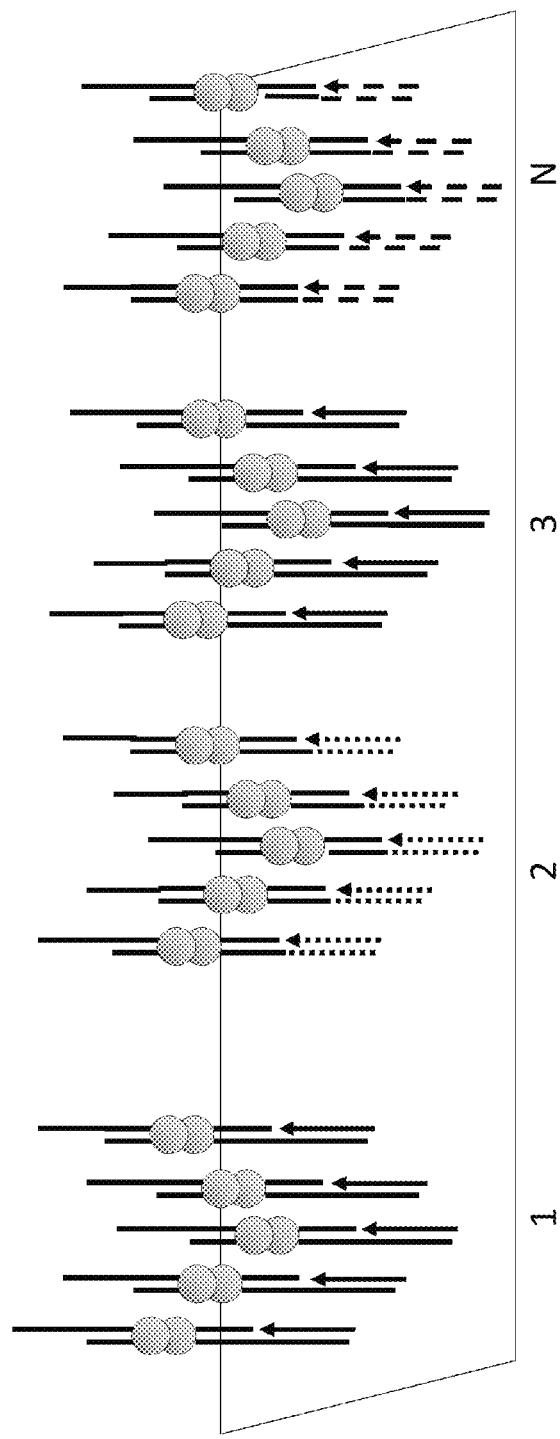
FIG. 4 is a drawing showing the transposase microarray generated from the combining/hybridization reaction shown in FIG. 3.

FIG. 3 depicts combining the transposase mixture of FIG. 2 with an array of oligonucleotide probes each specific for a first oligonucleotide domain having a unique barcode. Hybridization of the transposase complexes produces the transposase microarray shown in FIG. 4, i.e., an array with spatial segregation of the complexes in accordance with their respective barcodes. When loading the microarray, it can be useful to minimize the nuclease activity of the transposase to prevent it from cleaving the DNA duplex that forms on the transposase array. Thus, in some embodiments, the hybridization is performed in a buffer which lacks divalent cations (e.g., $Mn^{2+}$ and $Mg^{2+}$ ions), thus rendering the transposases inactive during this process (transposase needs divalent cations for enzymatic activity). For example, the mixture of transposase complexes can include a nuclease inhibitor, e.g., a divalent cation chelating agent. In other embodiments, a hybridization temperature below the active temperature for the transposase can be used to minimize cleavage activity. Once the transposase is loaded onto the array, a buffer exchange can be performed, as long as the temperature of the DNA duplex is kept above its melting temperature in the buffer of interest.

The resultant transposase array thus includes distinct regions that each have transposase complexes with the same barcode sequence. Arrays of oligonucleotide probes that are specific for a first oligonucleotide domain having a specific unique barcode can be synthesized on the microarray surface using any convenient method and can include a cleavable (optically or chemically) linker at or near the 3'-end. The design of barcodes and corresponding anti-barcode oligonucleotide probes is well within the skill in the art.

The transposase complexes on the array can be at a density of, inter alia, at least 1000 molecules per $\mu m^2$, e.g., at least 1000 molecules per $\mu m^2$, at least 5000 molecules per $\mu m^2$, at least 10,000 molecules per $\mu m^2$, at least 20,000 molecules per $\mu m^2$, at least 50,000 molecules per $\mu m^2$, up to 100,000 molecules per $\mu m^2$ or more. In certain embodiments, the areas that contain the transposase complexes should be substantially more hydrophilic than the surrounding surface such that the surrounding surface confines the aqueous fluid to the feature for a practical volume of fluid (that can be at a contact angle as low as 20-30 degrees). In such cases the aqueous fluid will have a surface energy below the critical surface energy for wetting with respect to the interfeature surface. The difference in hydrophobicity between the areas that contain the transposase complexes and the areas between the transposase complexes can be controlled by controlling the density of the transposase complexes, the lengths of the polymers, the linker chemistry and by selecting a substrate with suitable surface properties (or modifying a substrate so that it has suitable surface properties).

Figure 5:
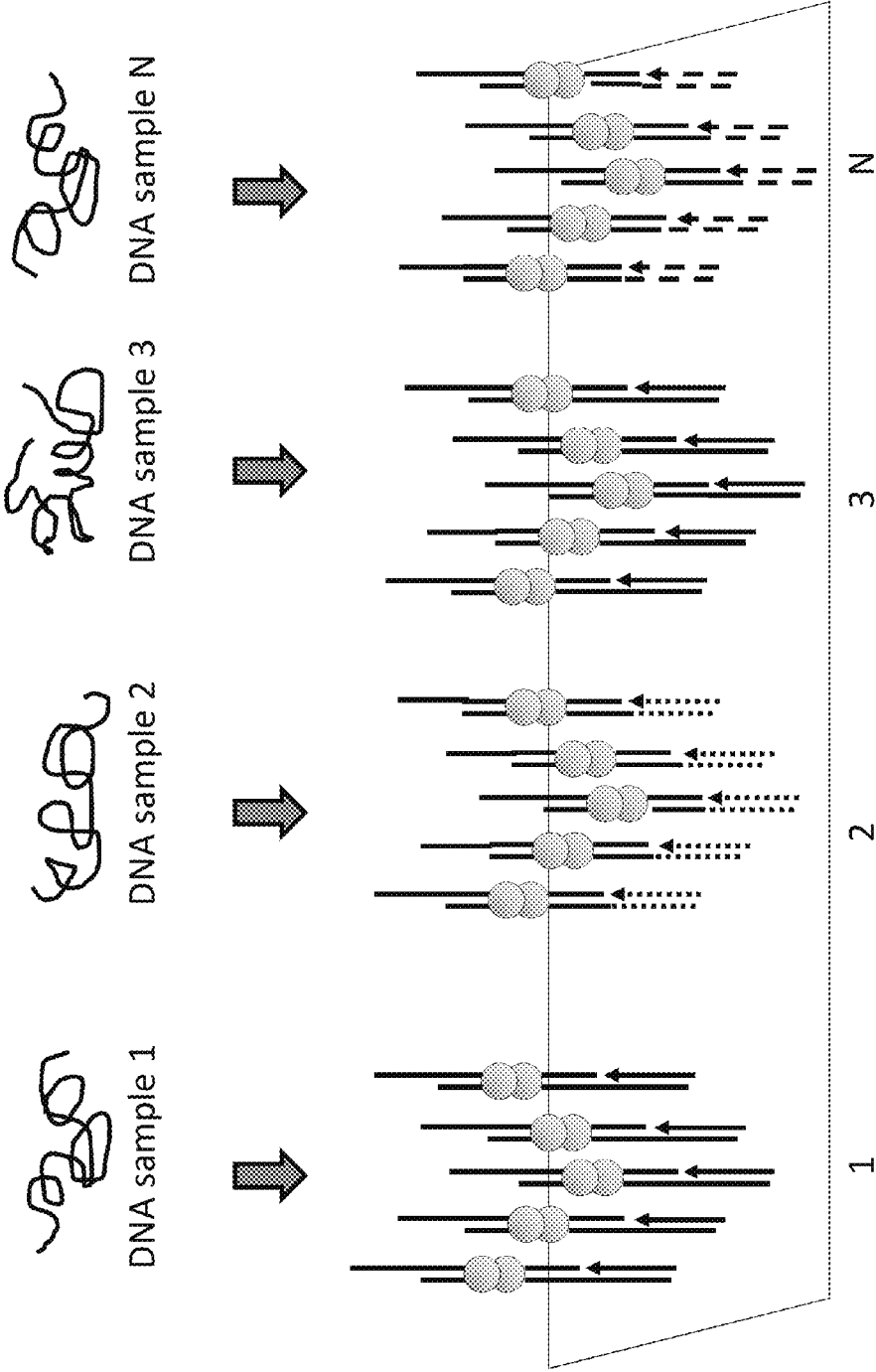
FIG. 5 is a drawing showing the delivery of different DNA samples to each different transposase complex on the transposase array shown in FIG. 4.

Once the transposase array is formed, individual DNA samples are delivered to each of the individual transposase features on the microarray together with buffer components necessary for transposase reaction (FIG. 5), (e.g., divalent cations $Mn^{2+}$ and/or $Mg^{2+}$, that render transposase active and the tagmentation reaction starts). The individual DNA samples can differ in any way desired by a user, e.g., from different individual cells, different tissues, different subjects, etc. In some embodiments, the different DNA samples each include a single DNA molecule to be tagged (e.g., a chromosomal fragment), whereas in other embodiments, each of the different DNA samples includes multiple DNA molecules. No limitation in this regard is intended.

Figure 6:
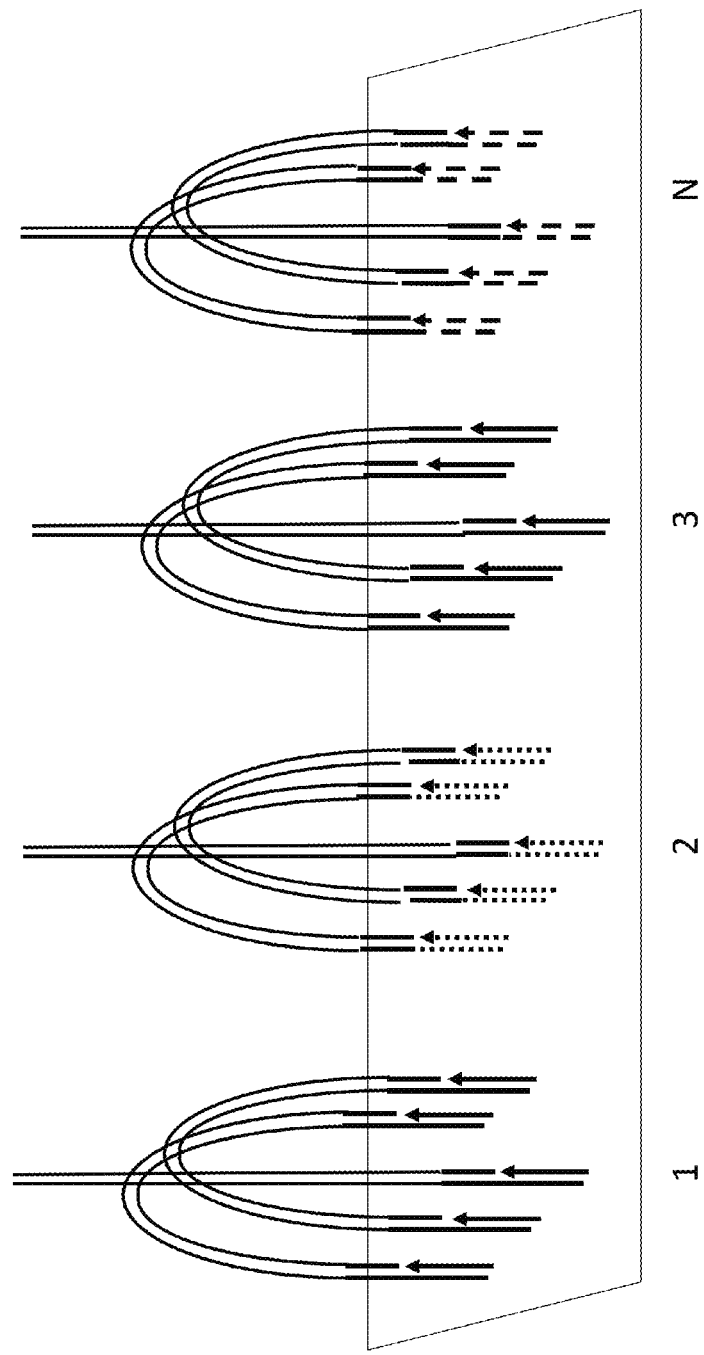
FIG. 6 is a drawing showing the resultant tagged (barcoded) DNA fragments attached to the substrate after delivery of the DNA in FIG. 5.

FIG. 6 shows the result of the tagmentation reaction after delivery of each of the DNA samples to their respective locations on the transposase array. In this figure, the DNA in each sample has been fragmented, and each end ligated to an adapter coupled to a transposase complex on the array surface. Because a single DNA molecule can be fragmented by more than one transposase complex, the target DNA can form bridges on the microarray surface, with each end covalently bound to an adapter domain that itself is bound via hybridization (DNA base-pairing) to complementary oligonucleotides attached to the substrate. Some DNA fragments can only be tagged once, and thus remain linear.

Figure 7:
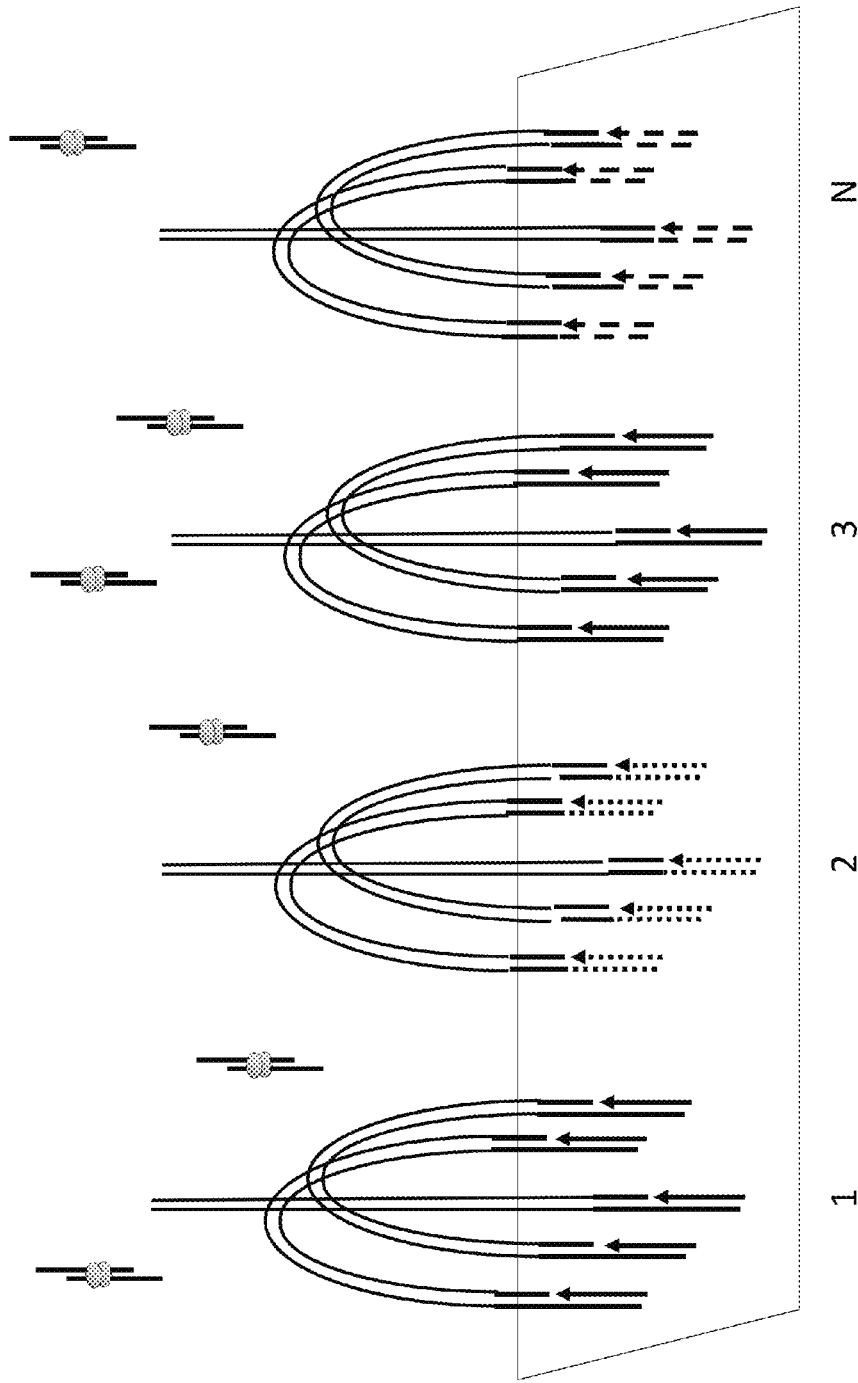
FIG. 7 is a drawing showing the addition of second transposase complexes to the barcoded DNA fragments attached to the substrate.
Figure 8:
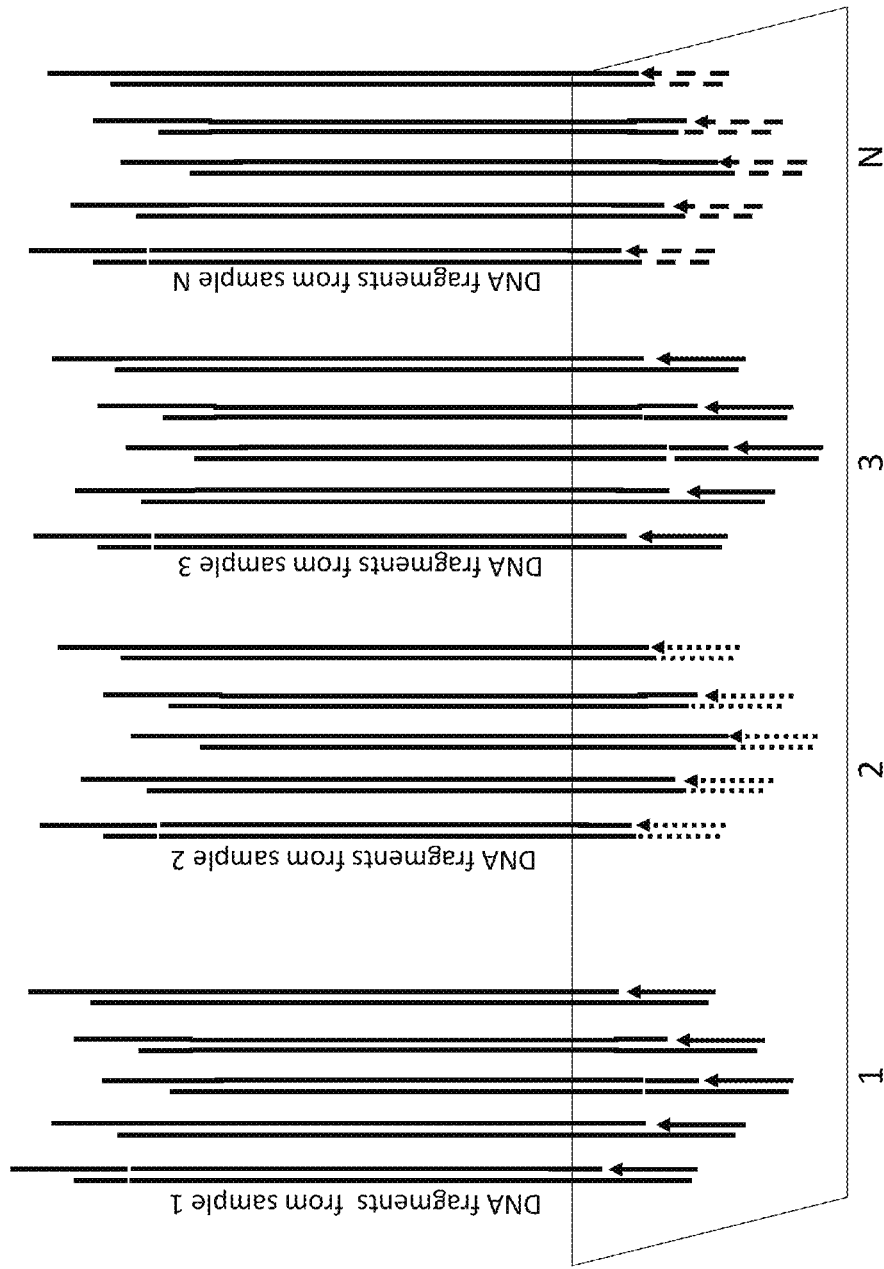
FIG. 8 is a drawing showing the linearized and barcoded DNA fragments attached to the substrate after addition of the second transposase complexes.

Contacting the surface-attached and tagged DNA (both linear and bridged forms) to second, solution-phase transposase complexes (as shown in FIG. 7) results in DNA that is tagged and attached to the substrate at one end and that also includes a second adapter sequence present on the free, non-surface-bound end (as shown in FIG. 8). This second transposase complex generally does not contain barcodes or other variable sequences. It is noted here that *Vibrio harveyi* transposase is active in wide range of incubation temperatures, i.e. 18-65° C. Thus, if microarrays are incubated after delivery of the DNA samples at a temperature which does not disrupt the hybridized oligonucleotides (i.e., between the first oligonucleotide domain region and the barcode specific oligonucleotide on the array), for example at room temperature for about 20-mer hybridized oligonucleotides, then the resulting DNA fragments remain attached to the microarrays. A benefit of this approach is that after performing transposase reaction, transposase buffer components can be removed by washes and substituted for PCR buffer components and PCR enzyme for subsequent amplification of the fragments in PCR. Such surface bound and tagged DNA fragments can be removed using any convenient method, e.g., heating, and used for downstream processes and/or analysis as described elsewhere herein. It is further noted that in some embodiments, the transposase complexes can be removed from the surface after delivery of the DNA sample but prior to tagging the DNA (not shown in FIG. 6). This can be accomplished in any convenient manner, e.g., heating the samples. Thus, while the tagged DNA fragments shown in FIG. 6 are still attached to the array, in some embodiments, the tagged DNA fragments are present in the solution phase.

Delivery of the DNA samples can be achieved in any convenient manner. For example, microfluidic channels can be used between two planar surfaces (one surface being the array, the other being microstructures) to guide each target DNA sample to its corresponding transposase complex-containing droplet. Samples can be moved to the appropriate features by means of pressure differentials, or positive displacement. In another embodiment, the motive force can be applied to droplets by optical tweezers or electrowetting. In yet another embodiment, a pattern of DNA sample droplets with a pattern that is complementary to the pattern of transposase complex droplets are brought into physical contact by moving two substrates together from opposite directions. No limitation in this regard is intended.

In some embodiments the DNA sample introduced to a corresponding transposase complex contains whole live or dead cells. In these embodiments, the cell membranes (outer wall and nuclear membrane) can be lysed by a number of distinct treatments, known to those skilled in the art. These treatments include the application of a lysing solution (usually basic) followed by the application of a neutralization solution. These reagents can be introduced to the sample droplets by the same means of applying the sample to the feature droplet. Another method for cell lysis is the application of high-power laser pulses that deliver heating energy to the cell causing cavitation and localized damage near and within the cell. Once the cell is lysed and the solution neutralized, the transposase complex droplet can be brought into contact with the DNA sample for barcoding.

In certain embodiments, the transposase complexes and DNA samples are combined as separate aqueous droplets present on independent solid substrates and then harvested for further analysis/processing as desired. The general process of aqueous droplet formation and harvesting (e.g., in emulsions) can be found in co-pending U.S. patent application Ser. No. 14/684,028, filed on Apr. 10, 2015 and entitled "Creating and Harvesting Surface-Bound Emulsion", hereby incorporated by reference herein in its entirety. One example of such a process is shown in FIGS. 7 to 10, described elsewhere herein.

Figure 9:
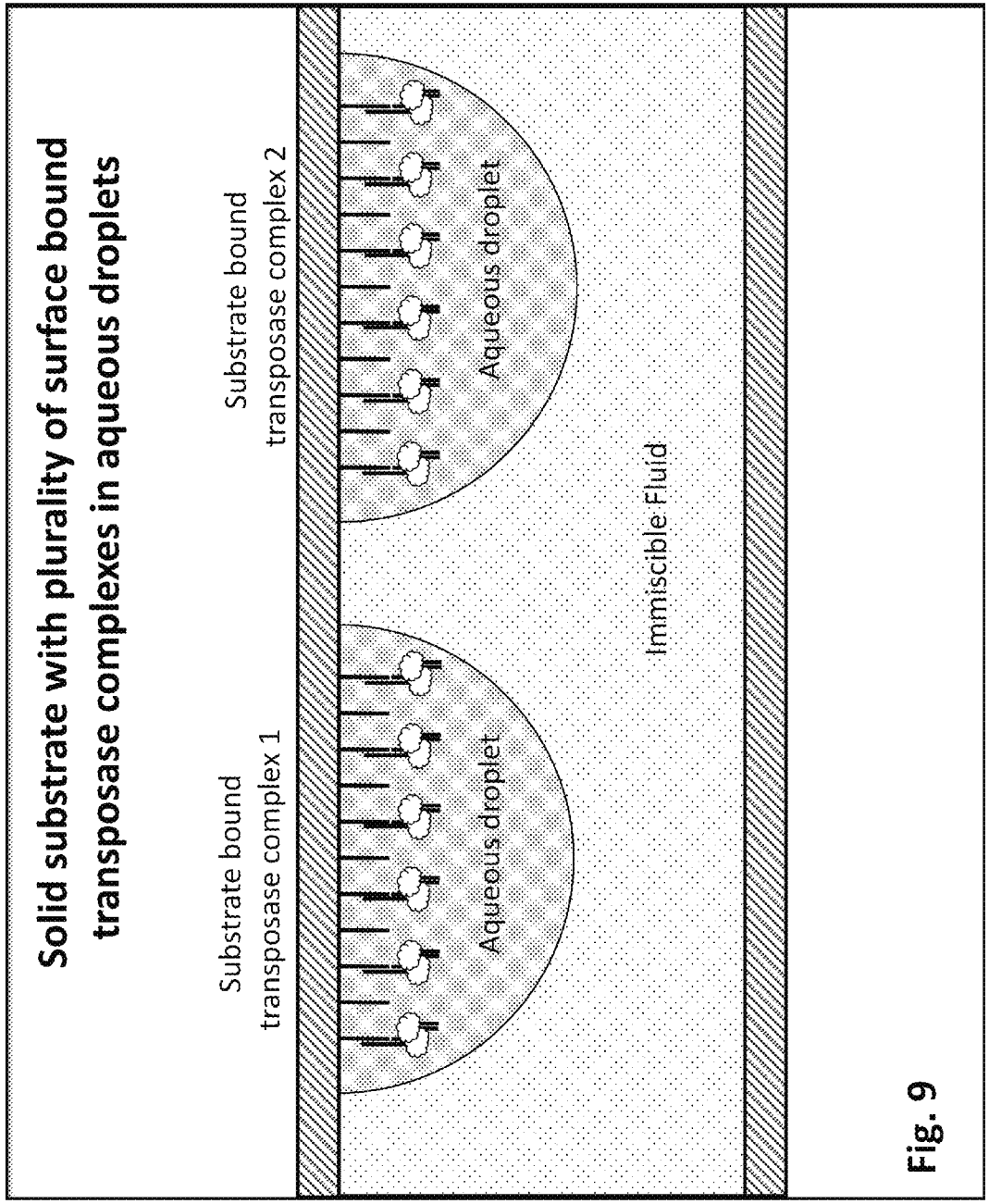
FIG. 9 is a drawing showing two substrate-bound transposase complexes according to one embodiment of the present disclosure. In this figure, transposase complexes 1 and 2 are bound to the first substrate (top) via hybridization to their corresponding oligonucleotide probes on the array and are each present in an aqueous droplet surrounded by an immiscible liquid (e.g., a hydrophobic liquid).

FIG. 9 shows two transposase complexes bound to a first substrate (a transposase microarray, top) each containing a first oligonucleotide domain having a unique barcode sequence. As shown, each of these complexes is present in their own distinct aqueous droplets which are surrounded by an immiscible liquid. Generating these droplets relies on the fact that the presence of the transposase complexes on the surface of the first substrate makes those areas hydrophilic relative to the remainder of the surface of the substrate, thereby allowing those areas to be selectively hydrated to produce discrete droplets on the surface of the substrate. After droplets have formed on the first substrate, an immiscible liquid is added to the substrate. Selectively hydrating can be done by any suitable method. In some embodiments, the selectively hydrating can be done by: placing the array in an environment having controlled humidity; b) printing a solution onto the areas that contain the compounds; c) subjecting the array to a freeze thaw cycle; or d) immersing the array in a solution and draining the solution from the areas that do not contain the compounds.

In certain embodiments, aqueous droplets are formed by condensation on the surface of an array of transposase complexes. In these embodiments, the array is enclosed in an environmentally-controlled chamber, where the temperatures of the surfaces and humidity of gases introduced are precisely controlled. An array of transposase complexes on the array surface provides regions that are hydrophilic. Water vapor is introduced into the sealed chamber containing the slides which then condenses preferentially on the hydrophilic features where the transposase complexes reside. By controlling the humidity, temperature and pressure of the chamber as well as independently controlling the temperature of the substrate itself, the formation of condensation can be precisely controlled. The hydrophilic transposase complexes features provide nucleation sites for the formation of water droplets. This process can be monitored and controlled by an automated vision system. The formation of undesirable parasitic droplets that are not localized to the features can be reduced by any one of several possible improvements. These improvements can include the integration of a resistive coating or electrodes onto the surface of the substrate in order to preferentially heat the surface area between the features, or the integration of a pattern of thermally conductive columns or wells into the underside of the substrate that cool the features relative to the regions surrounding them. In another approach the slide is cooled to a point where the water is allowed to freeze on the surface. This approach has been found to reduce the formation of parasitic droplets between features.

An alternative to the condensation method is to use an inkjet to deposit a droplet of aqueous solution directly onto each transposase complexes feature. The inkjet can rapidly fire droplets in precise patterns and cover the whole slide or wafer with droplets within minutes or even seconds. This droplet generation machinery is not as complex as an oligonucleotide writer, since all features get the same reagent and there is no immersion step. One complexity of this device is that the humidity will likely need to be controlled so that the droplets maintain their original sizes, without significant evaporation throughout the deposition process and until the next step. It can also be efficient to integrate this machine with an ammonia chamber for cleavage, to minimize wafer handling after cleavage.

This process can also be used to deposit DNA samples onto a substrate for combining with a transposase array (as described elsewhere herein and shown in FIGS. 10 to 13).

In additional embodiments, an array of spatially arranged droplets can be generated on an array by flooding a substrate with transposase complexes with aqueous reagent and eluting the reagent, leaving aqueous reagent behind on the hydrophilic regions where the transposase complexes reside. The same patterns can be achieved by dipping the slide into aqueous reagents. Typically, droplets formed in this by elution of a reagent are flat relative to their diameter due to the dynamics of the surface tension of the meniscus. The droplet volumes can be controlled and enhanced after formation by controlling the humidity and temperature of the environment. In this way, smaller droplets can be made larger by cooling the substrate and/or adding water vapor or cooling to condense vapor. Several parameters affect the volumes of the droplets as they form on the surface, the feature size of the hydrophobic region being the strongest factor, but other factors are involved as well, and these can be used to optimize the droplet volume during formation. These additional factors include: the surface tension of the aqueous media, the chemical composition, such as the ionic concentrations or polarities of the molecules in the media, the viscosity of the media, and the speed of the meniscus as it moves past the features. The chemical composition of the medium has a strong effect on a number of these parameters. Useful agents for modifying these parameters of reagents include, but are not limited to: water, glycerol, PEG (polyethylene glycol), salts, and surfactants.

After formation of the water droplets, an immiscible liquid can be applied to the surface to encapsulate the aqueous droplets. Where the surface of the solid substrate has been prepared to be oleophilic, the oily liquid will readily spread thinly across or "wet" the surface. The wetting of the whole surface can benefit by the use of multiple tips distributed across the surface, or by moving the tip or tips across the substrate. The substrate can also be tilted to enhance fluid flow across the slide housed within a chamber. Alternatively, the chamber can be flooded through an open orifice into the chamber. Alternatively, it can also be spin-coated, but at a speed that is low enough that the water droplets are not displaced by the centripetal force. In our preliminary experiments, we have experimentally found the droplets to be surprisingly robust with regard to flooding with oil.

The immiscible liquid can comprise a mineral oil such as Petroleum Special, an alkane such as heptadecane, a halogenated alkane such as bromohexadecane, carbonated oils, perfluorocarbon oil, e.g. 3M's Novek™ HFE-7500, an alkylarene, a halogenated alkylarene, an ether, or an ester having a boiling temperature above 100° C., for example. The immiscible liquid should be insoluble or only slightly soluble in water.

Figure 10:
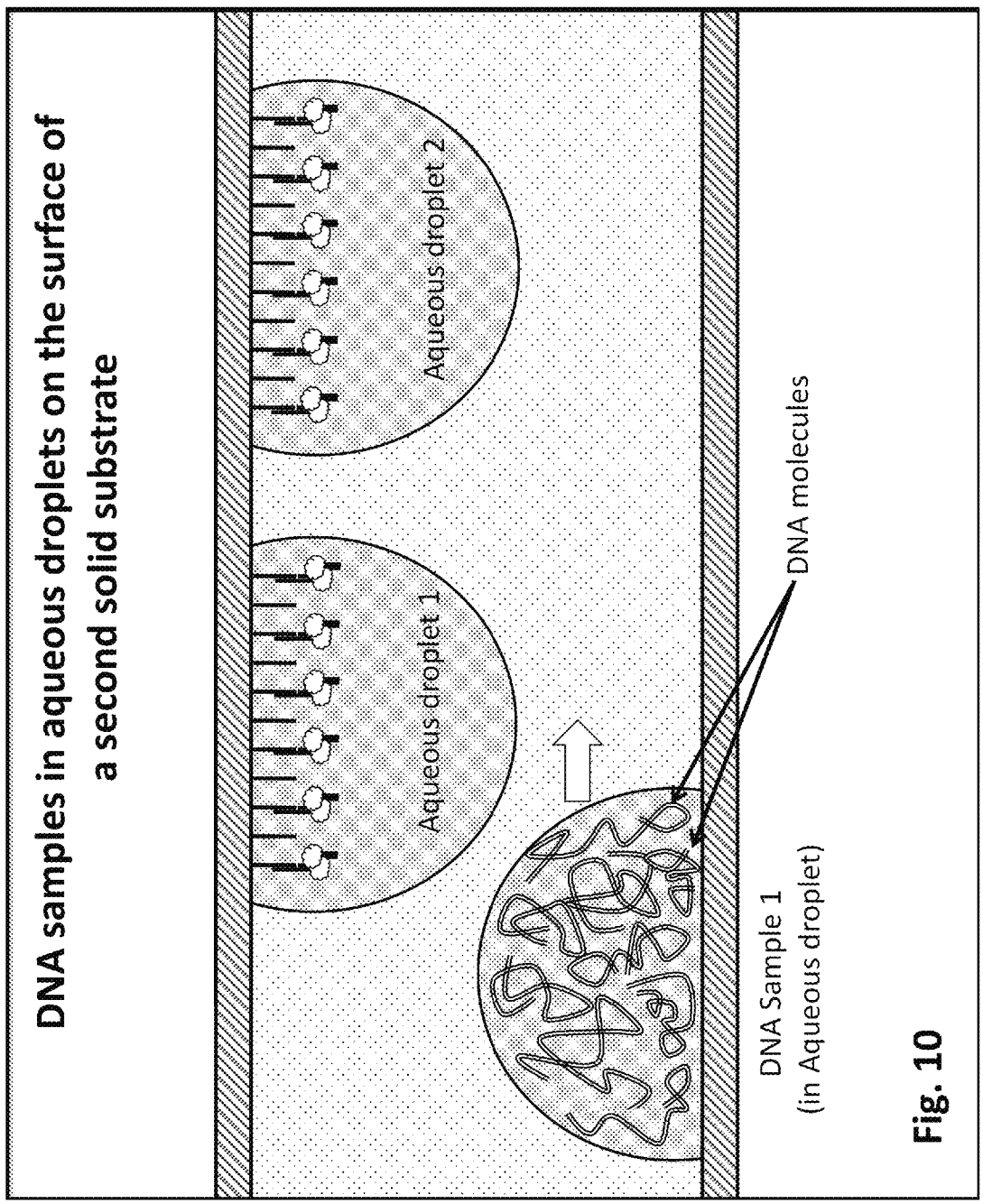
FIG. 10 is a drawing showing a first DNA sample in an aqueous droplet disposed on the surface of a second substrate (bottom) being moved into proximity with its corresponding transposase complex droplet.
Figure 11:
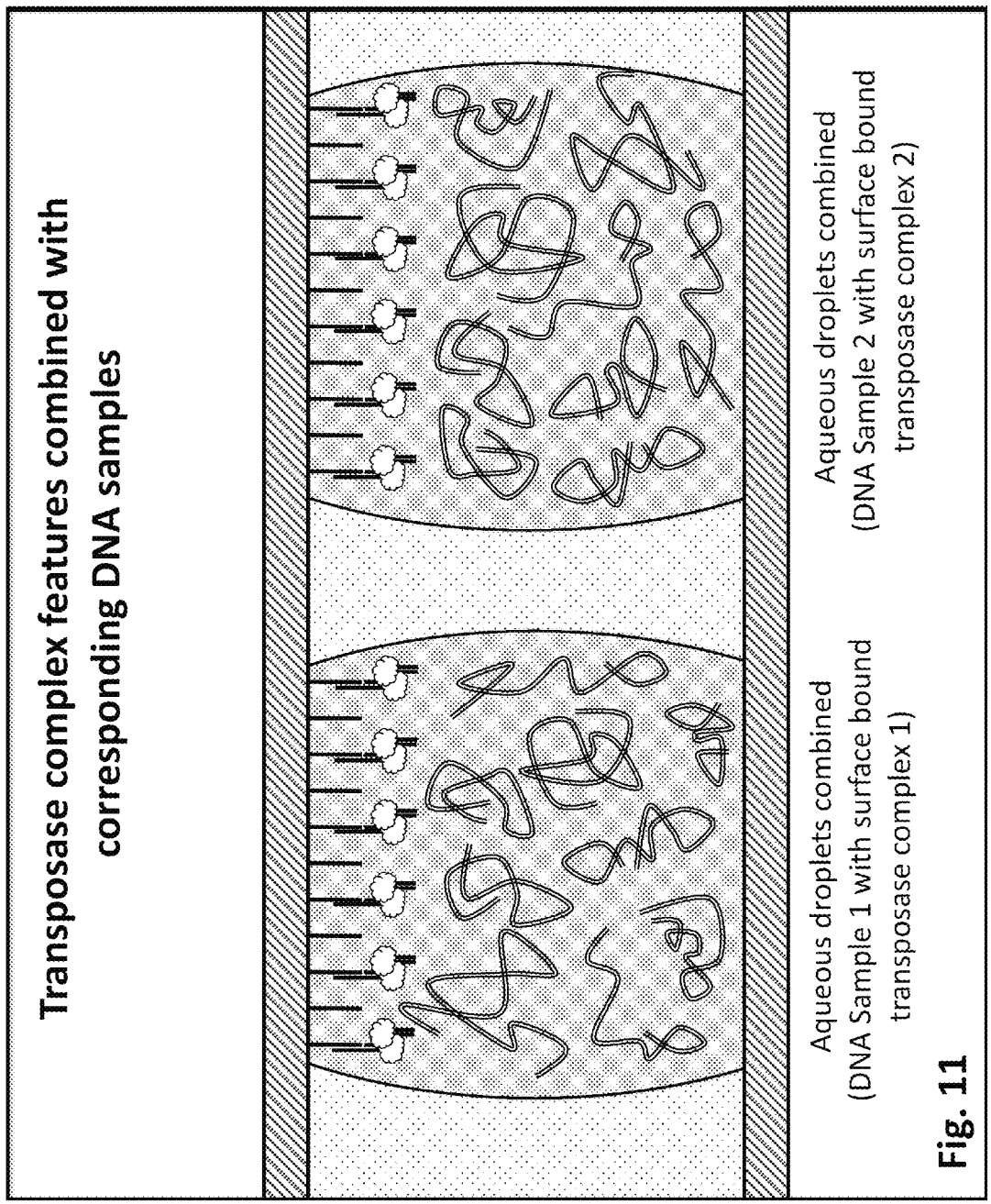
FIG. 11 is a drawing showing the result of combining two different DNA samples with their corresponding transposase complexes. The combined droplets are kept separate.
Figure 12:
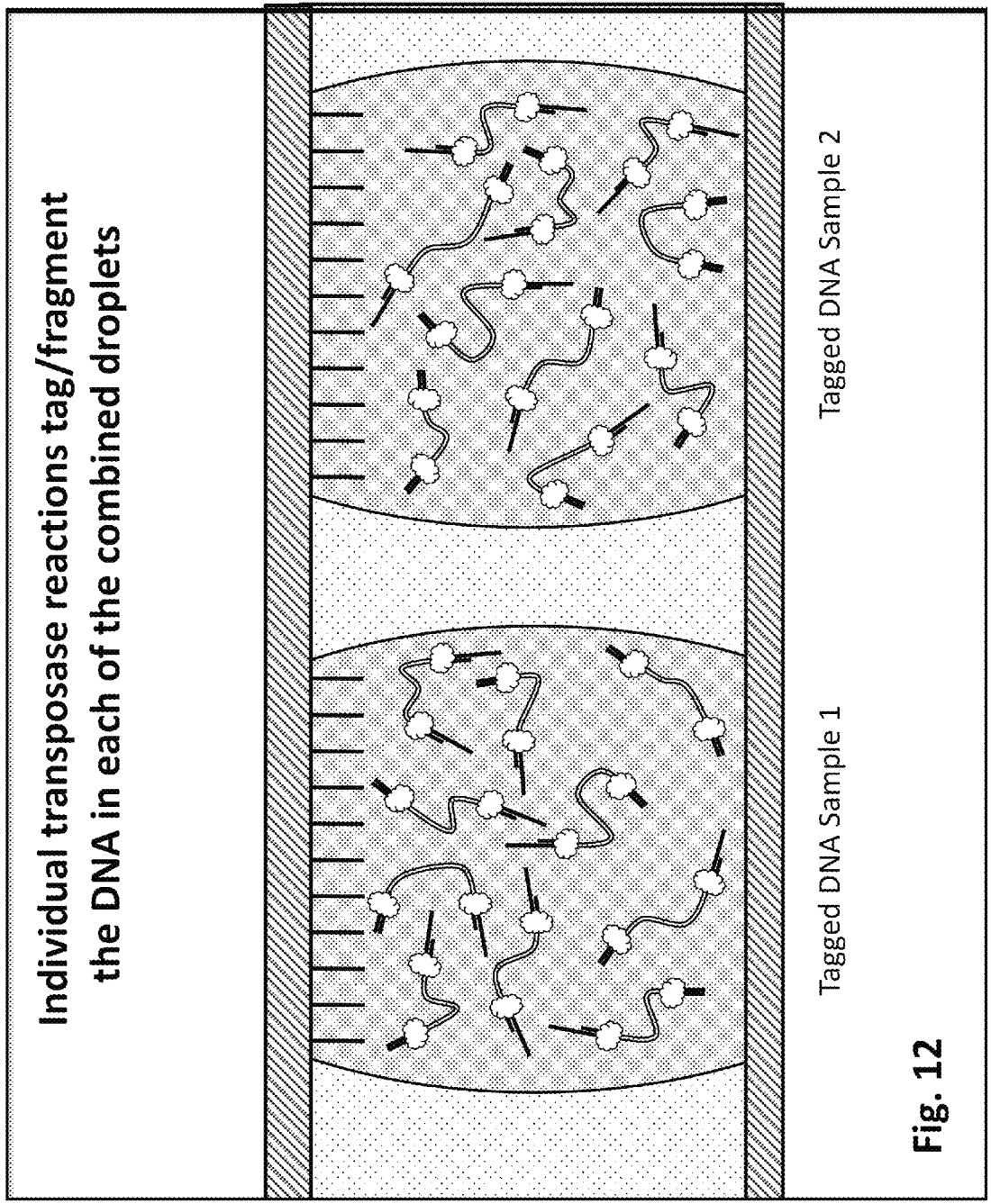
FIG. 12 is a drawing showing the fragments that are the result of the tagging/barcoding and fragmenting reaction in the combined aqueous droplets from FIG. 9.

In certain embodiments, a second solid substrate carrying a plurality of DNA samples to be tagged is brought into proximity to corresponding transposase complex features on an array of transposase complexes. For example, as shown in FIG. 10, a solid substrate carrying a DNA sample in an aqueous droplet (DNA sample 1; only one DNA sample is shown in FIG. 10) is brought into proximity to a corresponding transposase complex feature on a separate solid substrate which is also in an aqueous droplet (Aqueous droplet 1). When the corresponding DNA sample/transposase complex aqueous droplets come into contact, they are combined (shown in FIG. 11, in which two different combined DNA sample/transposase complex features are shown). This combining results in the tagging and fragmentation of the DNA in each of the plurality of DNA samples with its corresponding transposase complex (FIG. 12). In embodiments in which each transposase complex feature includes a different barcode sequence in the first oligonucleotide domain, each DNA sample will be uniquely tagged/barcoded. It is noted here that substrates carrying a plurality of DNA samples can be generated in any convenient manner (e.g., by inkjet deposition, multichannel pipettes, etc.) and, where desired, encapsulated in an immiscible liquid as described herein.

In FIG. 12, the tagged DNA is shown in solution. However, in certain embodiments the tagged DNA remains attached to the substrate. In such embodiments, the aqueous droplets and immiscible liquid can be removed from the attached tagged DNA, optionally washed (while maintaining the tagged DNA on the substrate), and then contacted with solution-phase transposase complexes to tag the DNA with a second oligonucleotide domain (see FIGS. 6 to 8, described elsewhere herein).

After the tagging reaction is complete, the droplets and their tagged DNA cargo can be harvested and combined in any convenient manner. In some embodiments, the droplets can be harvested from the substrate(s) by: a) moving a hydrophobic blade across the surface of the substrate(s), i.e., gently scraping the droplets off the surface of the substrate(s) using a blade; b) displacing the droplets laterally by applying a liquid shear force, e.g., by gently wiggling the array from side to side; c) displacing the droplets by centrifugation; d) causing the droplets to expand, e.g., using heat or negative pressure; e) cleaving the oligonucleotides to which the transposase complexes are hybridized (e.g., via a cleavable linker); f) firing a shaped acoustic or ultrasonic wave or pulse at the droplets; or g) aspirating the droplets from the surface using an aspirator that has a set of channels aligned with the droplets. Depending on the density of the droplets relative to the immiscible liquid, the droplets can rise or fall into the substrate.

After harvesting and combining the tagged/barcoded DNA, it can be subjected to any desired downstream process, e.g., amplification and/or NGS. For example, PCR amplification can be performed using a primer pair that includes a first primer specific for a primer binding site in the barcoded adapter and a second primer specific for a primer binding site in the non-barcoded adapter. Fragments with two different adapter sequences will be amplified while those with only one primer binding site will undergo suppression PCR (which substantially reduces the amplification). Other ways of isolating DNA fragment with different adapter sequences can be employed (e.g., using a 2-step hybridization method described elsewhere herein for isolation of transposase complex heterodimers).

Because each different tagged DNA sample contains a barcode indicative of its identity (the DNA in sample 1 is tagged with barcode 1, the DNA in sample 2 is tagged with barcode 2, etc.), it is possible to identify the source of the target DNA even when the tagged samples are combined and subsequently sequenced. Bioinformatic methods for determining the source of a nucleic acid based on a barcode sequence are commonly referred to as deconvolution.

For the purpose of applicability to next generation sequencing, it is preferred that about a half of the adapter ends are tagged with one type of tag and another half with a different tag, such that after transposase-mediated fragmentation of a target DNA, one kind of tag is attached to one end of the target DNA fragment, and another type to the opposite end to allow reading of a DNA fragment in both directions. Because the tagging reaction can generate any combination of tagged ends on the DNA (two of the same first tag, two of the same second tag, or the desired combination of one of each tag), it can be necessary to isolate and/or amplify the desired species (see description elsewhere herein).

Another aspect of the invention relates to kits. In general, kits according to the present invention comprise one or more components of at least one of the aspects of the invention described above that is useful for fragmenting and barcoding a plurality of DNA samples. The components of the kits can be provided in, or bound to, one or more solid materials. For example, one or more components can be provided in a container, which can be fabricated from plastic materials and formed in the shape of microfuge tubes or sequencing plates (e.g., 84- or 96-wells per plate). Alternatively, one or more components can be provided as a substance bound to a solid support. For example, a transposase complex can be provided as a complex bound on the surface of a transposase array (as described elsewhere herein). Alternatively, a mixture of uniquely barcoded transposase complexes can be provided. Those of skill in the art are aware of numerous other equivalent containment materials and forms that can be used to contain the components of kits.

In another embodiment of the kit of the invention, one or more oligonucleotide adapters are provided in one or more containers. The adapter can be provided as a liquid solution (e.g., an aqueous or alcohol solution) in one or more containers. Alternatively, the adapter can be provided as a dried composition in one or more containers. In embodiments, two or more different adapters can be provided in a single container or in two or more containers. Where two or more containers are provided, each container can comprise a single adapter, or one, some, or all of the containers can comprise a mixture of one, some, or all of the adapters.

As mentioned elsewhere herein, the kits of the invention can comprise any number of substances that are useful for practicing a method of the invention. Such substances include, but are not limited to: reagents (including buffers) for lysis of host cells, divalent cation chelating agents or other agents that inhibit nucleases, control DNA for use in ensuring that the transposase complexes and other components of reactions are functioning properly, DNA fragmenting reagents (including buffers), PCR reaction reagents (including buffers), and wash solutions.

The kits of the invention can be provided at any temperature. For example, for storage of kits containing transposases, adapters, or complexes in a liquid, it is preferred that they are provided and maintained below 0° C., preferably at or below −20° C., or otherwise in a frozen state.

As noted elsewhere herein, components of the kits are provided in containers or on solid substrates. The containers and solid substrates are provided in packaged combination in a suitable package, such as a box made of cardboard, plastic, metal, or a combination thereof. Suitable packaging materials for biotechnology reagents are known and widely used in the art, and thus need not be specified herein.

What is claimed is:

1. A method of tagging DNA in a plurality of DNA samples, the method comprising:
    (i) providing a first planar solid substrate comprising a plurality of spatially-addressable features, wherein each feature:
        (a) is in a separate aqueous droplet; and
        (b) comprises a transposase complex, wherein the transposase complex is bound to the surface of the first planar solid substrate and comprises a first oligonucleotide domain comprising a unique barcode sequence; and
    (ii) combining the plurality of features with one or more DNA samples that are on a second planar solid substrate, wherein the combining is done under conditions that permit transposase-mediated tagging of DNA,
    to produce a plurality of tagged DNA samples.

2. The method of claim 1, wherein the plurality of spatially-addressable features on the first solid substrate are encapsulated in an immiscible liquid.

3. The method of claim 2, wherein the immiscible liquid is a hydrophobic liquid.

4. The method of claim 1, wherein the transposase complex in each of the plurality of features is bound to the first solid substrate by hybridization of the first oligonucleotide domain to an oligonucleotide attached to the first solid substrate, wherein the oligonucleotide comprises a sequence complementary to the unique barcode sequence in the first oligonucleotide domain.

5. The method of claim 4, wherein the providing step (i) comprises:
    contacting a mixture of transposase complexes with first oligonucleotide domain sequences comprising different unique barcodes with a solid substrate comprising an array of barcode-specific oligonucleotide features under hybridization conditions, thereby producing a solid substrate comprising a plurality of features that each comprise a transposase complex.

6. The method of claim 5, wherein the mixture of transposase complexes comprises a nuclease inhibitor.

7. The composition of claim 6, wherein the nuclease inhibitor is a divalent cation chelating agent.

8. The method of claim 6, wherein the nuclease inhibitor is removed prior to the combining step (ii).

9. The method of claim 1, wherein each of the DNA samples is in an aqueous droplet.

10. The method of claim 9, wherein the combining step (ii) occurs in an immiscible liquid.

11. The method of claim 1, wherein each of the DNA samples is from a different source.

12. The method of claim 1, wherein each of the DNA samples is from a different cell.

13. The method of claim 1, further comprising harvesting and mixing the tagged DNA after the combining step (ii).

14. The method of claim 1, wherein each of the transposase complexes comprises:
    a first oligonucleotide component comprising a single-stranded region and a double-stranded region, wherein the single-stranded region comprises the first oligonucleotide domain comprising the unique barcode sequence and the double-stranded region comprises a transposase recognition sequence;
    a second oligonucleotide component comprising a single-stranded region and a double-stranded region, wherein the single-stranded region comprises a second oligonucleotide domain and the double-stranded region comprises a transposase recognition sequence; and
    a transposase enzyme dimer bound to the transposase recognition sequences of the first and second oligonucleotide components.

15. The method of claim 14, wherein the first oligonucleotide domain comprises a first primer binding site upstream of the unique barcode sequence and the second oligonucleotide domain comprises a second primer binding site.

16. The method of claim 15, further comprising amplifying the tagged DNA in the plurality of tagged DNA samples using a primer specific for the first primer binding site and/or the second primer binding site, wherein each of the amplified tagged DNA maintains its unique barcode sequence.

17. The method of claim 16, wherein the amplifying comprises performing a polymerase chain reaction (PCR) with a first and second primer specific for the first and second primer binding sites.

18. The method of claim 16, wherein the plurality of tagged DNA samples is combined prior to the amplification step.

19. The method of claim 15, further comprising sequencing one or more of the tagged DNA in the plurality of tagged DNA samples.

* * * * *